(12) United States Patent
Brunner et al.

(10) Patent No.: US 6,177,598 B1
(45) Date of Patent: Jan. 23, 2001

(54) PREPARATION OF SUGAR ALCOHOLS

(75) Inventors: Melanie Brunner, Schifferstadt; Boris Breitscheidel, Limburgerhof; Jochem Henkelmann, Mannheim; Arnd Böttcher, Frankenthal, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/283,866

(22) Filed: Apr. 1, 1999

(30) Foreign Application Priority Data

Apr. 7, 1998 (DE) .............................................. 198 15 639

(51) Int. Cl.[7] ..................... C07C 29/141; C07C 29/145; C07D 307/62
(52) U.S. Cl. ............................................ 568/863; 549/315
(58) Field of Search ............................................... 568/863

(56) References Cited

U.S. PATENT DOCUMENTS

| 4,380,680 | 4/1983 | Arena | ................................... 568/863 |
| 4,471,144 | 9/1984 | Arena | ................................... 568/863 |
| 4,487,980 | 12/1984 | Arena | ................................... 568/863 |

*Primary Examiner*—Bernard Dentz
(74) *Attorney, Agent, or Firm*—Oblon, Spivak, McClelland, Maier & Neustadt, P.C.

(57) ABSTRACT

A process for the hydrogenation of a sugar or a mixture of two or more thereof comprises the following step:

Bringing the sugar or the mixture of two or more thereof into contact with hydrogen in the presence of specific catalysts to give a sugar alcohol or a mixture of two or more thereof, wherein the catalyst comprises at least one metal of transition group VIII of the Periodic Table, either alone or together with at least one metal of transition group I or VII of the Periodic Table.

4 Claims, No Drawings

PREPARATION OF SUGAR ALCOHOLS

The present invention relates to a process for preparing sugar alcohols by hydrogenation of sugars using catalysts comprising one or more metals of transition group VIII of the Periodic Table as active component(s).

Sugar alcohols such as sorbitol, mannitol, maltitol and xylitol are widely used in the food industry, in cosmetics, in pharmacy and in the industrial sector.

Processes for preparing sugar alcohols from the corresponding sugars by hydrogenation, in particular batchwise processes in which pulverulent metal catalysts, e.g. nickel catalysts, are used in a suspension process, are known from the prior art (cf. Ullmanns Encykl. der Technischen Chemie, Vol. 24, p. 772 (1983)).

EP-A 0 773 063 describes a continuous process for the hydrogenation of sugars over a Raney Ni—Al catalyst at 130° C. and 150 bar.

Hydrogenations of sugars over supported Ru catalysts have likewise been described. U.S. Pat. No. 4,471,144 describes the hydrogenation of carbohydrates in aqueous solution in the presence of a ruthenium-on-$\theta$-$Al_2O_3$ catalyst. U.S. Pat. No. 4,487,980 describes a similar process in which a catalyst comprising a metal of transition group VII and $TiO_2$ as support is used. U.S. Pat. No. 4,380,680 describes the use of a supported catalyst comprising $\alpha$-$Al_2O_3$ as support and a metal selected from among Os, Ru, Pd and Pt as active component in the hydrogenation of sugars to give sugar alcohols.

A study of the deactivation of the catalysts used which occurs in such hydrogenations is described, using the hydrogenation of glucose using Ru on $Al_2O_3$ as catalyst as an example, in a scientific article in Applied Catalysis A: General 87 (1992), pp. 219–229.

Although, as can be seen from the above summary of the prior art, a number of processes for the hydrogenation of sugars are already known, the catalysts used hitherto not infrequently have short operating lives as a result of deactivation or "bleeding" of the catalyst. Furthermore, noticeable epimerization, decomposition or polymerization of the sugar alcohols frequently occurs during the hydrogenation under the conditions selected.

It is an object of the present invention to provide new processes for the hydrogenation of sugars in which specific catalysts comprising one or more metals of transition group VIII of the Periodic Table as active metal are used. These new processes should make it possible, in particular, to obtain virtually epimer-free sugar alcohols in very high yields at a virtually complete conversion. Furthermore, only a minimal proportion of by-products or decomposition products compared to the conventional processes should be formed during the hydrogenation so as to enable a subsequent work-up of the sugar alcohols to be carried out in a simple and economical manner.

We have found that this object is achieved by, in one embodiment of the present invention, a process for the hydrogenation of a sugar or a mixture of two or more thereof, which comprises the following step:

Bringing the sugar or the mixture of two or more thereof into contact with hydrogen in the presence of a catalyst to give a sugar alcohol or a mixture of two or more thereof, wherein the catalyst comprises at least one homogeneous compound of at least one metal of transition group VIII of the Periodic Table, either alone or together with at least one metal of transition group I or VII of the Periodic Table, deposited in situ on a support (catalyst 1).

In a further embodiment, the present invention provides a process for the hydrogenation of a sugar or a mixture of two or more thereof, which comprises the following step:

Bringing the sugar or the mixture of two or more thereof into contact with hydrogen in the presence of a catalyst to give a sugar alcohol or a mixture of two or more thereof, wherein the catalyst comprises as active metal at least one metal of transition group VIII of the Periodic Table, either alone or together with at least one metal of transition group I or VII of the Periodic Table, in an amount of from 0.01 to 30% by weight, based on the total weight of the catalyst, applied to a support, where from 5 to 50% of the pore volume of the support is made up by macropores having a pore diameter in the range from 50 nm to 10,000 nm and from 50 to 95% of the pore volume of the support is made up by mesopores having a pore diameter in the range from 2 to 50 nm, where the sum of the pore volumes is 100% (catalyst 2).

The present invention also provides a process for the hydrogenation of a sugar or a mixture of two or more thereof, which comprises the following step:

Bringing the sugar or the mixture of two or more thereof into contact with hydrogen in the presence of a catalyst to give a sugar alcohol or a mixture of two or more thereof, wherein the catalyst is a monolithic supported catalyst which can be produced by successive heating and cooling in air of a support material in the form of a metal mesh or a metal foil, subsequent coating under reduced pressure with an active component and subsequent cutting and shaping of the coated support material and final processing to give a monolithic supported catalyst, where the active metal used is at least one metal of transition group VIII of the Periodic Table, either alone or together with at least one metal of transition group I or VII of the Periodic Table (catalyst 3).

As active metal, it is in principle possible to use any metal of transition group VIII of the Periodic Table. Preference is given to using platinum, rhodium, palladium, cobalt, nickel or ruthenium or a mixture of two or more thereof as active metal, with particular preference being given to using ruthenium as active metal. As the metals of transition group I or VII or else I and VII of the Periodic Table which can also be used, preference is given to using copper and/or rhenium, although any of them can be used in principle.

For the purposes of the present invention, the terms "macropores" and "mesopores" are used as they are defined in Pure Appl. Chem., 45, p. 79 (1976), namely as pores whose diameter is above 50 nm (macropores) or whose diameter is from 2 nm to 50 nm (mesopores).

The active metal content is generally from about 0.01 to about 30% by weight, preferably from about 0.01 to about 5% by weight and in particular from about 0.1 to about 5% by weight, in each case based on the total weight of the catalyst used. In the case of the catalysts 1 to 3, preferred contents are again indicated individually in the discussion of these catalysts.

If customary catalyst support systems, e.g. activated carbon, silicon carbide, aluminum oxide, silicon dioxide, titanium dioxide, zirconium dioxide, magnesium oxide, zinc oxide or mixtures thereof, are used for producing the catalysts used according to the present invention, they are in each case used in spherical, extrudate or ring form if they are to be used as fixed-bed catalysts and as grit or fine granules for use in suspension. Further details regarding these support systems may be found in the discussion of the individual catalysts 1 to 3.

For the purposes of the present invention, it is in principle possible to use any sugar. The term "sugar" used in the context of the present invention encompasses monosaccharides such as glucose, mannose, galactose, talose, fructose, allose, altrose, idose, gulose, xylose, ribose, arabinose, lyxsose, threose and erythrose, disaccharides and trisaccharides such as maltose, lactose, cellobiose, sucrose, melibiose and raffinose, and polysaccharides such as starch, starch decomposition products, cellulose and cellulose decomposition products, e.g. dextrin, glucose syrup, cellulose hydrolysates and starch hydrolysates such as maize starch hydrolysates.

In the processes of the present invention, preference is given to converting glucose into sorbitol, mannose into mannitol, fructose into a mixture of sorbitol and mannitol, xylose into xylitol, lactose into lactitol and maltose into maltitol.

Catalyst 1

The process of the present invention can be carried out in the presence of a catalyst 1 which comprises at least one homogeneous compound of at least one metal of transition group VIII of the Periodic Table deposited in situ on a support, if desired together with at least one homogeneous compound of at least one metal of transition group I or VII of the Periodic Table. The catalysts are produced by introducing a homogeneous metal compound into the reactor together with the feed during the reaction so that this compound is, during the reaction, deposited onto a support present in the reactor.

The homogeneous metal compound can also be introduced into the reactor prior to the reaction and be deposited onto a support present in the reactor during a treatment with hydrogen.

The term "in situ" used in the context of the present application means that the catalyst is not prepared and dried separately and then introduced into the reactor as a finished catalyst, but rather the catalyst is, for the purposes of the present invention, formed in the reactor either immediately before or during the actual hydrogenation.

The term "homogeneous compound of a metal of transition group VIII, I or VII of the Periodic Table" or "homogeneous ruthenium compound" used in the context of the present application means that the metal compound used according to the present invention is soluble in the surrounding medium, i.e. in the aqueous solution of the sugar still to be hydrogenated.

Metal compounds which can be used here are, in particular, nitrosyl nitrates and nitrates, but also halides, carbonates, carboxylates, acetylacetonates, chloro, nitrito and amine complexes and also hydrated oxides or mixtures thereof. Preferred compounds are ruthenium nitrosyl nitrate, ruthenium (III) chloride, ruthenium (III) nitrate and hydrated ruthenium oxide.

Although the amount of metal compound applied to the support or supports in the process of the present invention is not restricted in any particular way, from the points of view of sufficient catalytic activity and the economics of the process the metal salt or metal complex is applied to the support or supports in such amounts that from 0.01 to 30% by weight, based on the total weight of the catalyst, of active metal is deposited on the support or supports. This amount is more preferably from 0.2 to 15% by weight, particularly preferably about 0.5% by weight.

The supports present in the reactor are preferably metal meshes or metal rings or steatite bodies, as are described, inter alia, in EP-A-0 564 830 and EP-A-0 198 435. Nevertheless, the supports which are particularly preferably used for the purposes of the present invention and their production will be briefly described below.

Particular preference is given to using metallic support materials such as the stainless steels having material numbers 1.4767, 1.4401, 2.4610, 1.4765, 1.4847, 1.4301, etc., since their surface can be roughened by heat treatment before coating with the active components. Very particular preference is given to using Kanthal (material No. 1.4767) or metals comprising aluminum as mesh material. Kanthal is an alloy which comprises about 75% by weight of Fe, about 20% by weight of Cr and about 5% by weight of Al. For the heat treatment, the abovementioned metallic supports are heated in air at from 600 to 1100° C., preferably from 800 to 1000° C., for from one to twenty hours, preferably for from one to ten hours, and then cooled again. This pretreatment is critical for the activity of the catalyst, since without this heat treatment virtually no ruthenium can be deposited in situ onto the metallic support. After this heat treatment at elevated temperature, the supports are coated with the ruthenium compound.

In a further preferred embodiment, the above-described supports can have a layer of a platinum metal, e.g. Ni, Pd, Pt, Rh, preferably Pd, vapor-deposited onto them in a thickness of from about 0.5 to about 10 nm, in particular about 5 nm, as is likewise described in the abovementioned EP-A-0 564 830.

In particular, the catalyst support used for the purposes of the present invention is a mesh made of heat-treated Kanthal on which a Pd layer having a thickness of about 5 nm has been vapor-deposited to aid the deposition of the active metal.

However, it is also possible to use customary catalyst support systems such as activated carbon, silicon carbide, aluminum oxide, silicon dioxide, titanium dioxide, zirconium dioxide, magnesium oxide, zinc oxide or mixtures thereof, in each case in spherical, extrudate or ring form or as grit or fine granules. Among these, particular preference is given to aluminum oxide and zirconium dioxide. The pore size and the pore size distribution is completely noncritical. It is possible to use bimodal and all other types of supports. The supports are preferably macroporous.

Further details regarding the catalyst 1 and its production may be found in DE-A 196 22 705.4 which is equivalent to U.S. Pat. No. 5,902,916, and whose contents relating to this subject are fully incorporated by reference into the present application.

Catalyst 2

The catalysts 2 used according to the present invention comprise one or more metals of transition group VIII of the Periodic Table as active component(s) on a support, as defined herein. Preference is given to using ruthenium, palladium and/or rhodium as active component(s).

The catalysts 2 used according to the present invention can be produced industrially by applying at least one active metal of transition group VIII of the Periodic Table, preferably ruthenium or palladium, and, if desired, at least one metal of transition group I or VII of the Periodic Table to a suitable support. Application can be achieved by immersing the support in aqueous metal salt solutions such as ruthenium or palladium salt solutions, by spraying appropriate metal salt solutions onto the support or by other suitable methods. Suitable metal salts for preparing the metal salt solutions are the nitrates, nitrosyl nitrates, halides, carbonates, carboxylates, acetylacetonates, chloro complexes, nitrito complexes or amine complexes of the corresponding metals, with preference being given to the nitrates and nitrosyl nitrates.

In the case of catalysts which have a plurality of active metals applied to the support, the metal salts or metal salt solutions can be applied simultaneously or in succession.

The supports coated or impregnated with the metal salt solution are subsequently dried, preferably at from 100° C. to 150° C. If desired, these supports can be calcined at from 200° C. to 600° C., preferably from 350° C. to 450° C. The coated supports are subsequently activated by treatment in a gas stream comprising free hydrogen at from 30° C. to 600° C., preferably from 100° C. to 450° C. and in particular from 100° C. to 300° C. The gas stream preferably consists of from 50 to 100% by volume of $H_2$ and from 0 to 50% by volume of $N_2$.

If a plurality of active metals are applied to the support and the application is carried out in succession, the supports can be dried at from 100° C. to 150° C. and, if desired, calcined at from 200° C. and 600° C. after each application or impregnation. The metal salt solutions can be applied in any order.

The metal salt solution or solutions is/are applied to the support or supports in such an amount that the active metal content is from 0.01 to 30% by weight, preferably from 0.01 to 10% by weight, more preferably from 0.01 to 5% by weight and in particular from 0.3% to 1% by weight, based on the total weight of the catalyst.

The total surface area of metal on the catalyst is preferably from 0.01 to 10 $m^2$/g, particularly preferably from 0.05 to 5 $m^2$/g and more preferably from 0.05 to 3 $m^2$/g, of the catalyst. The metal surface area is measured by the chemisorption method as described in J. LeMaitre et al., "Characterization of Heterogeneous Catalysts", Edited by Francis Delanney, Marcel Dekker, New York (1984), pp. 310–324.

In the catalyst 2 pused according to the present invention, the ratio of the surface areas of the active metal or metals and the catalyst support is less than about 0.3, preferably less than about 0.1 and in particular about 0.05 or less, with the lower limit being about 0.0005.

The support materials which can be used for producing the catalysts 2 used according to the present invention possess macropores and mesopores.

The supports which can be used according to the present invention have a pore size distribution in which from about 5 to about 50%, preferably from about 10 to about 45%, more preferably from about 10 to about 30% and in particular from about 15 to about 25%, of the pore volume is made up by macropores having pore diameters in the range from about 50 nm to about 10,000 nm and from about 50 to about 95%, preferably from about 55 to about 90%, more preferably from about 70 to about 90% and in particular from about 75 to about 85%, of the pore volume is made up by mesopores having a pore diameter of from about 2 to about 50 nm, where in each case the sum of the pore volumes is 100%.

The total pore volume of the supports used according to the present invention is from about 0.05 to 1.5 $cm^3$/g, preferably from 0.1 to 1.2 $cm^3$/g and in particular from about 0.3% to 1.0 $cm^3$/g. The mean pore diameter of the supports used according to the present invention is from about 5 to 20 nm, preferably from about 8 to about 15 nm and in particular from about 9 to about 12 nm.

The surface area of the support is preferably from about 50 to about 500 $m^2$/g, more preferably from about 200 to about 350 $m^2$/g and in particular from about 250 to about 300 $m^2$/g of the support.

The surface area of the support is determined by the BET method by $N_2$ adsorption, in particular in accordance with DIN 66131. The mean pore diameter and the size distribution are determined by Hg porosimetry, in particular in accordance with DIN 66133.

Although all support materials known in catalyst production which have the above-defined pore size distribution can be used in principle, preference is given to using activated carbon, silicon carbide, aluminum oxide, silicon dioxide, titanium dioxide, zirconium dioxide, magnesium oxide, zinc oxide or mixtures thereof, more preferably aluminum oxide and zirconium dioxide.

Further details regarding catalyst 2 and its production may be found in DE-A 196 24 485.4, which is equivalent to pending U.S. application Ser. No. 08/877,820, and whose contents relating to this subject are fully incorporated by reference into the present application.

Catalyst 3

The catalyst 3 used according to the present invention can be produced by heating the support material in the form of a metal mesh or a metal foil in air, cooling it and then coating it under reduced pressure with the above-described active metal or the combination of two or more thereof, subsequently cutting and shaping the coated support material and finally processing it to form a monolithic catalyst element. This catalyst and its production have already been comprehensively described in EP-A-0 564 830 and U.S. Pat No. 4,686,202, whose contents relating to this subject are fully incorporated by reference into the context of the present application. In the following, only the essential basic steps for producing this catalyst or the preferred embodiments thereof will be briefly discussed. As regards the active metals used, what has been said for catalysts 1 and 2 applies.

Particularly well suited metallic support materials in the form of metal foils or metal meshes are stainless steels such as those having the material numbers 1.4767, 1.4401, 2.4610, 1.4765, 1.4847, 1.4301, etc., since their surface can be roughened by heat treatment before coating with active components. For this purpose, the metallic supports are heated in air at from 600 to 1100° C., preferably from 800 to 1000° C., for from 1 to 20 hours, preferably from 1 to 10 hours, and cooled again. This pretreatment is critical for the activity of the catalyst. After this heat treatment at elevated temperature, the support is coated with the active compound. For this purpose, the support is coated with the active component(s), either simultaneously or in succession, batchwise or continuously, at a pressure of from $10^{-3}$ to $10^{-5}$ mbar by means of a vapor deposition apparatus, e.g. an electron beam vaporization or a sputtering apparatus. For activation of the catalyst, this can be followed by heat treatment under inert gas or air.

In producing the catalyst layers as described here, the aim is to produce disorders and disrupted polycrystalline layers or clusters. For this reason, particularly good vacuum conditions are not normally necessary. Furthermore, the active components can be obtained in very finely crystalline or cluster form by alternate vapor deposition of active components and structural promoters.

The catalyst can here be built up systematically, for example in a vapor deposition unit using a plurality of different vaporization sources. Thus, for example, an oxide layer or a bonding layer can first be applied to the support by reactive vapor deposition. Active components and promoters can be applied to this "primer" layer in a plurality of alternate layers. Admission of a reactive gas into the vapor deposition chamber enables promoter layers of oxides or other compounds to be produced. Heat treatments can also be intercalated.

As a result of this method of producing the catalyst mesh or the catalyst foils, the active components adhere so well that the mesh or foil can be cut, shaped and processed to form monolithic catalyst elements.

A very simple monolithic catalyst is obtained by shaping the catalyst mesh or the catalyst foil by means of a toothed roller and then rolling together smooth and corrugated mesh or foil to produce a cylindrical monolith having similar vertical channels. However, it is also possible to fashion any static mixers from this catalyst material, since the adhesion of the catalyst layer is sufficiently high.

The resulting monolithic catalyst elements in the form of mixing elements are installed in a reactor and a reaction liquid to be reacted is brought into contact with them.

Carrying Out the Process

In the processes of the present invention, the hydrogenation is generally carried out at from about 50 to about 140° C., preferably from about 80 to about 120° C. The pressures used are generally above about 50 bar, preferably from about 80 to about 300 bar, particularly preferably from about 100 to about 160 bar. The processes of the present invention can be carried out either continuously or batchwise, with preference being given to a continuous process. In a continuous process, the respective catalysts can be used as fixed-bed catalysts or in suspension. The catalysts used according to the present invention are preferably used as fixed-bed catalysts. In the suspension method, the processes of the present invention are preferably carried out in a reactor which incorporates a fitting which has openings or channels having a hydraulic diameter of 0.5 to 20 mm, preferably from 1 to 10 mm and in particular from 1 to 3 mm, known as a bubble column. Further details regarding this specific reactor may be found in DE-A 196 11 976, which is equivalent to U.S. Pat. No. 5,939,589 and whose contents are fully incorporated by reference into the context of the present application.

In a continuous process, the amount of sugar to be hydrogenated is from about 0.05 to about 3 kg/l of catalyst per hour, more preferably from about 0.1 to about 1 kg/l of catalyst per hour.

Hydrogenation gases used can be any gases which comprise free hydrogen and contain no deleterious amounts of catalyst poisons such as CO. For example, it is possible to use waste gases from a reformer. Preference is given to using pure hydrogen as hydrogenation gas.

The sugars to be reacted are used in pure form as aqueous solutions. The concentration of the sugar is preferably from about 15 to about 70% by weight, more preferably from about 30 to about 55% by weight, based on the total weight of the aqueous solution.

The pH of the aqueous solution is generally from about 3.5 to about 10, preferably from about 3.5 to about 8. Owing to slight contamination by sugar acids, the aqueous sugar solutions are generally neutral or slightly acid. They can be adjusted to the desired pH in a manner known to those skilled in the art. In principle, the hydrogenation of the sugars can also be carried out without altering the pH, in which case a later, possibly complicated, removal of the substances which have been used for adjusting the pH becomes unnecessary.

In the processes of the present invention, the conversion of the sugars in the hydrogenation is virtually complete. A maximum of 0.1% by weight of the sugar used was able to be detected in the product solution. The sugar alcohols are obtained in virtually epimer-free form, i.e. the epimer content of the product is generally not more than 1% by weight, preferably not more than 0.5% by weight, and in high purity (>99%). The heavy metal content is generally less than 10 ppm, preferably less than 5 ppm and in particular less than 1 ppm.

The present invention accordingly provides, in particular, for the use of the processes described herein for preparing sugar alcohols which are virtually epimer-free.

The product solutions which are obtained at the end of the hydrogenation and which contain the desired sugar alcohol(s) can, if desired, be concentrated by customary methods, e.g. spray drying, freeze drying, rolling dry or evaporation.

In any case, they can be further processed in concentrated or unconcentrated form without further purification steps.

The sugar alcohols obtained in this way, in particular sorbitol, can be used as food additives, in particular as sweeteners, humectants in foodstuffs and in cosmetics and pharmaceutical products, as raw materials for the production of polyurethanes, in particular for producing rigid polyurethane foams.

The sorbitol prepared according to the present invention can be used, in particular, for the synthesis of vitamin C.

The present invention therefore also provides a process for synthesizing vitamin C starting from sorbitol, wherein the sorbitol starting material is obtained by one of the processes described herein.

The processes of the present invention or the use of the catalysts described herein in the hydrogenation of sugars to give sugar alcohols bring, in particular, the advantage that no significant traces of metals in colloidal or ionic form, as can arise, for example, from decomposition or "bleeding" of the catalysts in particular as a result of the chelating effect of the polyhydroxy compounds, can be detected in the sugar alcohols obtained in the hydrogenation. The metal contents of the raw products are generally not more than 1 ppm. This eliminates the need to remove the heavy metals from the respective sugar alcohols obtained as raw product, as is necessary in numerous processes of the prior art. The processes are thus far simpler, cheaper and more environmentally friendly, The sugar alcohols obtained as raw products generally meet the commercial purity conditions, for instance according to the German pharmacopoeia (DAB), Food Chemical Codex (FCC) or Joint Experts Committee on Food Additives (JECFA), and therefore require no further purification before further processing, for example in the food sector.

The present invention is illustrated by the example below.

EXAMPLE

Production of Catalyst

A mesoporous/macroporous aluminum oxide support in the form of 4 mm extrudates, which had a BET surface area of 238 $m^2/g$ and a pore volume of 0.45 ml/g, was impregnated with an aqueous ruthenium (III) nitrate solution having a concentration of 0.8% by weight. 0.15 ml/g (about 33% of the total pore volume) of the pores of the support had a diameter in the range from 50 nm to 10,000 nm and 0.30ml/g (about 67% of the total pore volume) of the pores of the support had a pore diameter in the range from 2 to 50 nm. The solution volume taken up during impregnation of the support corresponded approximately to the pore volume of the support used.

The support which had been impregnated with the ruthenium (III) nitrate solution was subsequently dried at 120° C. and activated (reduced) at 200° C. in a stream of hydrogen. The catalyst produced in this way contained 0.5% by weight of ruthenium, based on the weight of the catalyst.

Hydrogenation of Glucose 7 g of the Ru catalyst as described in the above example were placed in a catalyst basket insert in a 300 ml pressure reactor and 150 g (0.42 mol) of a 50% strength by weight glucose solution (pH=5.5) were added. The hydrogenation was carried out using pure hydrogen at a constant pressure of 150 bar and a temperature of 100° C. Hydrogenation was continued until no more hydrogen was taken up (10 h). The reactor was subsequently vented. The glucose conversion was 99.95%. The yield of sorbitol was 99.1%, the yield of mannitol was about 0.5%, in each case based on the total amount of glucose used. The ruthenium content of the sugar alcohols obtained was less than 1 ppm.

We claim:

1. A process for the hydrogenation of a sugar or a mixture of two or more thereof, which comprises the following step:

Bringing the sugar or the mixture of two or more thereof into contact with hydrogen in the presence of a catalyst to give a sugar alcohol or a mixture of two or more thereof, wherein the catalyst comprises as active metal at least one metal of transition group VIII of the Periodic Table, either alone or together with at least one metal of transition group I or VII of the Periodic Table, in an amount of from 0.01 to 30% by weight, based on the total weight of the catalyst, applied to a support, where from 5 to 50% of the pore volume of the support is made up by macropores having a pore diameter in the range from 50 nm to 10,000 nm and from 50 to 95% of the pore volume of the support is made up by mesopores having a pore diameter in the range from 2 to 50 nm, where the sum of the pore volumes is 100%.

2. A process as claimed in claim 1, wherein the sugar is selected from the group consisting of glucose, mannose, fructose, xylose, lactose, maltose and mixtures of two or more thereof.

3. A process as claimed in claim 1, wherein the catalyst is present as a fixed bed and the process is carried out continuously.

4. A process for synthesizing vitamin C starting from sorbitol, which comprises the following step:

Preparing sorbitol from glucose by means of a process as claimed in claim 1.

* * * * *